United States Patent [19]

Hall, Jr. et al.

[11] 4,225,735

[45] Sep. 30, 1980

[54] ISOMERIZATION OF THE HYDROGENATED NORBORNADIENE ENDO-ENDO HEXACYCLIC DIMER

[75] Inventors: Lewis W. Hall, Jr., Chadds Ford, Pa.; John D. Tice, Wilmington, Del.; Harry K. Myers, Jr., Aston; Abraham Schneider, Overbrook Hills, both of Pa.

[73] Assignee: Suntech, Inc., Philadelphia, Pa.

[21] Appl. No.: 7,113

[22] Filed: Jan. 29, 1979

[51] Int. Cl.$^2$ .................... C07C 13/28; C07C 15/12
[52] U.S. Cl. ......................... 585/360; 60/208; 149/109.4; 585/362; 585/671; 585/666
[58] Field of Search ............... 585/666, 671, 360, 362

[56] References Cited

U.S. PATENT DOCUMENTS

| | | | |
|---|---|---|---|
| 3,558,733 | 1/1971 | Myers | 585/671 |
| 3,655,798 | 4/1972 | Csicsery | 585/666 |
| 3,879,310 | 4/1975 | Rigge | 585/671 |
| 4,086,286 | 4/1978 | Janoski | 585/360 |

OTHER PUBLICATIONS

T. J. Katz et al., Tetrahedron Letters, No. 27, 2601–2605, 1967.
Nancy Acton et al., J. Am. Chem. Soc. 94, 15, 1972.
Chem. Ab., 91:87128q, 1969.
H. A. Quinn et al., J. Catalyst 26, 333–337, 1972.
M. N. Aktor, J. Amer. Chem. Soc. 96, 276–277, 1974.

*Primary Examiner*—Veronica O'Keefe
*Attorney, Agent, or Firm*—J. Edward Hess; Donald R. Johnson; Anthony Potts, Jr.

[57] ABSTRACT

Isomerization of a liquid, saturated endo-endo norbornadiene hexacyclic dimer involves the use of a catalytic amount of acidic alumina or a montmorillonite. The resulting isomeric product is solid, at ambient temperature, and can be used as a missile fuel.

4 Claims, No Drawings

ISOMERIZATION OF THE HYDROGENATED NORBORNADIENE ENDO-ENDO HEXACYCLIC DIMER

BACKGROUND OF THE INVENTION

The invention herein described was made in the course of or under a contract with the United States Air Force Systems Command.

This invention relates to the isomerization of a saturated endo-endo dimer of norbornadiene, hereinafter referred to as HNN. Particularly the invention relates to the preparation of a solid isomeric mixture from liquid HNN involving a catalyst.

The aforementioned solid isomeric mixture can be used as a high energy missile fuel in either jet or rocket propulsion or as an additive for other similar mixtures. Jet propulsion includes a jet engine which can be used for a missile, an aircraft and others and includes the three basic types, i.e. ramjet, turbojet and pulse jet. The term rocket generally refers to a device containing fuel incorporating its own oxygen or oxidizing agent.

Norbornadiene (bicyclo-(2.21.1)-2,5-heptadiene) can be prepared by reacting cyclopentadiene and acetylene at an elevated temperature, see U.S. Pat. No. 2,875,256 (Cl 260-666). Norbornadiene has the following structure:

It can be dimerized into an olefinic endo-endo homo dimer having the following structure:

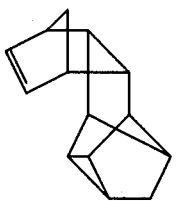

I

Dimerization of norbornadiene to compound I is disclosed in "The Stereochemical Course of Metal Catalyzed Cycloaddition Reactions of Norbornadiene", T. J. Katz et al, Tetrahedron Letters, No. 27, pp 2601-2605, 1967. The dimerization involves the use of a group VIII metal complex. Compound I is also disclosed in Chemical Abstracts, 91: 1, Jan. 1, 1969, page 265, 87128q. The dimerization is also disclosed in "Dimerization and Trimerization of Norbornadiene by Soluble Rhodium Catalysts", Nancy Acton et al, Journal of the American Chemical Society, 94:15, July 26, 1972.

The olefinic bond of compound I can be hydrogenated. Generally a hydrogenation catalyst such as 5% rhodium-on-alumina is satisfactory. The temperature and pressure used for hydrogenation can be mild, e.g. about 125° C. and 100 psig of hydrogen. The saturated endo-endo dimer of norbornadiene (HNN) has the following structure:

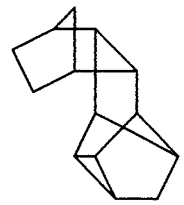

II

Related work in catalytic isomerization of dimers of norbornadiene are reported in Journal of Catalyst 26, 333-337, 1972, "Skeletal Rearrangement of Some Cyclic Hydrocarbons Catalyzed by Palladium", H. A. Quinn et al; Journal of the American Chemical Society, 96:1, Jan. 9, 1974, "Hydrogenolysis of Substituted Nortricyclenes over Supported Metal Catalyst Methyl Migrations and Skeletal Rearrangements," M. N. Aktar et.al. Both of the foregoing involve the use of metals such as platinum or palladium as a catalyst.

SUMMARY OF THE INVENTION

Isomerization of liquid HNN occurs when using a catalytic amount of an acidic alumina or a montmorillonite and the temperature of the reaction is at an isomerization temperature. The resulting mixture contains at least one solid isomer having a molecular weight equal to HNN and at least one solid oligomer.

DESCRIPTION

The isomerization of liquid HNN to a solid (at ambient temperature) mixture can be represented by the following:

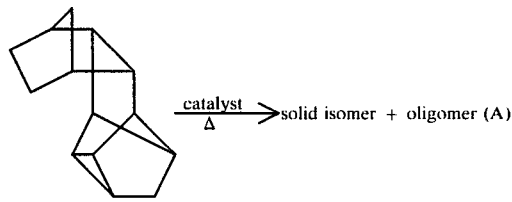

II

The oligomer is the result of several monomer units of HNN joining together to form a low molecular weight polymer.

The catalyst can be any one of the particular clays of the montmorillonite family. The montmorillonite mineral family is known, for example see Encyclopedia of Chemical Technology, Kirk-Othmer, 2nd Edition, Vol. 5, Clays (survey). A preferred montmorillonite is bentonite and more preferred is an acidic bentonite. The catalyst can also be an acidic alumina. The properties and preparation of alumina (aluminum oxide) are well known, for example see Kirk-Othmer, Encyclopedia of Chemical Technology, 2nd Edition, Vol. 2, Aluminum Compounds. Alumina has many different phases and can be one of the following: alpha or beta trihydrate, alpha or beta monhydrate, alpha, gamma, delta, eta, theta, iota, kappa, or chi. Small amounts of other materials, e.g. silica, can be present in the alumina. An acidic alumina is an alumina that has been washed or prepared in an acidic environment. The acid used to form the environment can be sulfuric, hydrochloric, phosphoric and the like. While any of the aforementioned aluminas can be used for the isomerization reaction a preferred alumina is acidic alpha monohydrate.

The amount of catalyst causing the isomerization is a catalytic amount. Thus the amount of acidic alumina or montmorillonite present is sufficient to direct the isomerization. However while a wide range of concentration can be used the preferred catalyst concentration range is between from about one part by weight of catalyst per hundred parts by weight of HNN, or feed, to about a one to one ratio while a more preferred ratio range is between from about 1:20 to about 1.5.

The isomerization temperature is one at which the isomerization reaction will occur and generally can vary between two general limits. A lower limit can be determined by the rate of the reaction, i.e. if the temperature is too low the reaction rate is slow, and a slow rate can make the process unattractive commercially. Thus, generally the lower temperature is about 20° C. with 50° C. preferred and 75° C. more preferred. The upper temperature limit can be determined by the formation of undesirable materials which adversely affect the properties of the isomeric mixture. Generally, the upper temperature limit is about 300° C. with 250° C. preferred and a more preferred limit is about 200° C.

While the HNN feed can contain other similar hydrocarbons, such hydrocarbons should not adversely affect the activity of the catalyst. Further, the similar hydrocarbons should not adversely influence the desired resulting properties of the product mixture. Thus, for optimum results, the feed can consist essentially of HNN.

After the isomerization, i.e. the forming of the solid mixture, the catalyst can be separated by various known means, e.g. hot filtration or decantation from the hydrocarbon product. The hydrocarbon product can be separated from any unreacted feed by high resolution capillary gas chromatography. Need for the separation of the product hydrocarbons depends on the specifications set for the missile fuel.

The following Examples illustrate the invention .

EXAMPLES

The HNN dimer, 18.6 g, was mixed in an Erlenmeyer flask with 1.86 g of acidic alumina (alpha-monohydrate), at room temperature and blanketed with argon. The flask was placed in a 192° C. stirred oil bath. After about 315 minutes the heating and stirring were discontinued. During the heating the alumina became a light tan-orange color. Conversion, as determined by vapor phase chromotography (vpc) was 93% and product selectivity as to the isomer was 97%. Conversion as used herein indicates the amount of the HNN which reacted to form products while selectivity indicates what portion of the formed products is a particular product. Mass spectroscopy indicated one isomer had a mass of 186 (which was identical with the starting dimer). This isomer was present in the largest amount. The hydrocarbon present, in the next largest amount, the oligomer, had a mass of 390. The hydrocarbon present in the third largest amount had a mass of 203. Thermal gravimetric analysis (TGA) indicated the presence of about 2% wt. of a polymer having a boiling point greater than 270° C. The solid product after drying, had a melting point between 52°-60° C. It was also determined that the isomer contained a cyclopropane ring structure.

In another run 18.6 g of the HNN dimer were mixed in an Erlenmeyer flask with 1.86 g of acidic non-swelling bentonite, a member of the montmorillonite family, under a blanket of argon. (A non-swelling bentonite is a calcium bentonite containing aluminum silicate.) The flask containing the mixture was placed in a 70° C. oil bath. After 10 minutes the temperature of the contents of the flask reached 69° C. and the color of the mixture was an orange-tan. The color of the mixture changed to a dark maroon. With intermittent heating and cooling the contents of the flask were at a temperature of 62°-69° C. for a total time of about 372 minutes. A solid product was formed and it had a mass of 186. Conversion, as determined by vpc was 39.5% with product selectivity as to the isomerized dimer of about 42.3%. Analysis by TGA indicated that only a small amount (2-4%) of any oligomer was formed with essentially no polymer.

Use of other acidic aluminas or other montmorillonites will yield analogous results.

The invention claimed is:

1. Process for the isomerization of a saturated endo-endo norbornadiene hexacyclic dimer comprising contacting a hexacyclic dimer having the following structure:

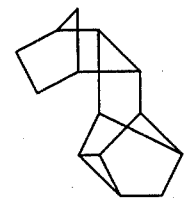

with a catalytic amount of acidic alumina or a montmorillonite at an isomerization temperature until an isomer is formed.

2. Process according to claim 1 wherein the isomerization temperature is in the range between from about 20° C. to about 300° C.

3. Process according to claim 1 wherein the montmorillonite is an acidic bentonite.

4. Process according to claim 1 wherein the isomer formed is a solid at an ambient temperature.

* * * * *